United States Patent
Faessler et al.

(10) Patent No.: US 10,112,886 B2
(45) Date of Patent: Oct. 30, 2018

(54) METHOD FOR PURIFICATION OF BENZOIC ACID

(71) Applicant: Sulzer Chemtech AG, Winterthur (CH)

(72) Inventors: Peter Faessler, Allschwil (CH); Manfred Stepanski, Buchs (CH)

(73) Assignee: Sulzer Chemtech AG, Winterthur (CH)

( * ) Notice: Subject to any disclaimer, the term of this patent is extended or adjusted under 35 U.S.C. 154(b) by 179 days.

(21) Appl. No.: 15/311,078

(22) PCT Filed: May 20, 2015

(86) PCT No.: PCT/EP2015/061179
§ 371 (c)(1),
(2) Date: Nov. 14, 2016

(87) PCT Pub. No.: WO2015/185361
PCT Pub. Date: Dec. 10, 2015

(65) Prior Publication Data
US 2017/0107167 A1    Apr. 20, 2017

(30) Foreign Application Priority Data

Jun. 2, 2014 (EP) .................................. 14170844

(51) Int. Cl.
*C07C 51/44* (2006.01)
*C07C 51/43* (2006.01)
(Continued)

(52) U.S. Cl.
CPC .............. *C07C 51/44* (2013.01); *B01D 3/141* (2013.01); *B01D 3/143* (2013.01); *B01D 9/0059* (2013.01);
(Continued)

(58) Field of Classification Search
CPC ......... C07C 51/00; C07C 51/42; C07C 51/43; C07C 51/44; C07C 51/46; B01J 19/24; B01D 3/141; B01D 3/143; B01D 9/0059
See application file for complete search history.

(56) References Cited

U.S. PATENT DOCUMENTS 2,471,134 A    5/1949    Wright
3,472,630 A    10/1969   Baldwin et al.
(Continued)

FOREIGN PATENT DOCUMENTS

CN    102942433 A    2/2013
DE    1443155 A1    4/1969
(Continued)

OTHER PUBLICATIONS

Jiao, X. et al. "Development on the Technique of Total Recovery of Benzoic Acid" Chinese Journal of Chemical Engineering, 2009, pp. 608-612, vol. 17, No. 4.
(Continued)

*Primary Examiner* — Brian A McCaig
(74) *Attorney, Agent, or Firm* — Larson & Anderson, LLC (57) ABSTRACT

The present invention relates to a method for purifying a crude benzoic acid (32) containing 5 to 20% by weight of byproducts and 80 to 95% by weight of benzoic acid, by means of distillation, wherein the distillation is performed in a plant comprising a first distillation system (54), which comprises a divided wall column (10). Preferably, the divided wall column (10) comprises: an upper portion having an upper undivided section (12) for concentrating low-boiling components, wherein the low-boiling components have a lower boiling point than benzoic acid, and an outlet for removal of the low-boiling components from the column (10), a lower portion having a lower undivided section (14) for concentrating high-boiling components, wherein the high-boiling components have a higher boiling point than benzoic acid, and an outlet for removal of the high-boiling components from the column (10), and a central portion arranged between the upper portion and the lower portion having at least one vertical dividing wall (20)

(Continued)

for dividing the central portion into at least one feed section (16) and at least one withdrawal section (18), the feed section (16) having an inlet for the feed of crude benzoic acid (32) and the withdrawal section having a side draw outlet for the purified benzoic acid (34).

18 Claims, 4 Drawing Sheets

(51) Int. Cl.
*B01J 19/24* (2006.01)
*B01D 9/00* (2006.01)
*B01D 3/14* (2006.01)
*C07C 51/265* (2006.01)
*C07C 51/00* (2006.01)
*C07C 51/42* (2006.01)
*C07C 51/46* (2006.01)

(52) U.S. Cl.
CPC .............. *B01J 19/24* (2013.01); *C07C 51/265* (2013.01); *C07C 51/43* (2013.01); *B01J 2219/24* (2013.01)

(56) References Cited

U.S. PATENT DOCUMENTS

| | | |
|---|---|---|
| 4,230,533 A | 10/1980 | Giroux |
| 6,958,111 B2 | 10/2005 | Rust et al. |
| 7,090,748 B2 | 8/2006 | Kaibel et al. |
| 7,108,770 B2 | 9/2006 | Grun et al. |
| 7,118,653 B2 | 10/2006 | Brady et al. |
| 7,169,267 B2 | 1/2007 | Kaibel et al. |
| 7,267,746 B1 | 9/2007 | Harris et al. |
| 7,342,134 B2 | 3/2008 | Knoesche et al. |
| 8,461,356 B2 | 6/2013 | Windecker et al. |
| 2011/0139604 A1 | 6/2011 | Burst et al. |
| 2011/0168542 A1 | 7/2011 | Schmidt et al. |
| 2012/0103013 A1 | 5/2012 | King et al. |

FOREIGN PATENT DOCUMENTS

| | | |
|---|---|---|
| DE | 10002810 A1 | 7/2001 |
| WO | 2013043606 A1 | 3/2013 |
| WO | 2014052298 A2 | 4/2014 |

OTHER PUBLICATIONS

Schultz, M. et al. "Reduce Costs with Dividing-Wall Columns" CEP, May 2002, pp. 64-71.

METHOD FOR PURIFICATION OF BENZOIC ACID

The present invention relates to a method for the purification of benzoic acid.

Benzoic acid, which is the structurally simplest aromatic carboxylic acid, has found widespread application in various sectors of industry. For example, benzoic acid is an important intermediate in chemical industry, which is used for example as a precursor for the preparation of phenol and benzoates, i.e. esters of benzoic acid. For instance, the diesters of ethylene glycol, diethylene glycol or triethylene glycol with benzoic acid are used as plasticizers in polymer compositions. In addition, certain esters of benzoic acid, such as methyl benzoate and ethyl benzoate, are used as fragrances in perfumes and cosmetics. Another important property of benzoic acid and salts formed thereof is their impact on microorganisms. Since these compounds inhibit the growth of fungi, yeast and specific bacteria, benzoic acid and its salts are used as preservatives in food, tobacco, cosmetic products and toiletries. Due to its fungistatic and bacteriostatic effect, benzoic acid also finds application as a pharmaceutical agent in the therapy of fungal skin diseases and as an antiseptic.

As a consequence of its manifold applications, the production of benzoic acid has been continuously increased and is estimated to have reached a current world production of 900 to 1,100 kilotons per year.

A commonly used method for the industrial preparation of benzoic acid is the oxidation of toluene with oxygen, wherein the methyl side chain of the toluene is converted into a carboxylic acid group. This process is by way of example performed making use of air as oxygen source in the presence of a transition metal catalyst. However, various byproducts are formed during the production of benzoic acid. Therefore, a purification of the crude benzoic acid is usually required after the reaction in order to obtain a purified product, which fulfills the specification for the desired further application. Known processes for the preparation of purified benzoic acid include for example distillation and crystallization.

A known method for the purification of crude benzoic acid is a distillation method, which is performed in a plant comprising two distillation columns arranged in series. Such a two-column distillation system is, for example, described in U.S. Pat. No. 3,472,630 and in DE 1 443 155. In accordance with one alternative, a feed of crude benzoic acid prepared by oxidation of toluene is introduced into the first distillation column. While the low-boiling components, i.e. those having a lower boiling point than benzoic acid, are separated and drawn off at the column head, a stream enriched with benzoic acid is drawn off at the column bottom product of the first distillation column and is fed to the inlet of the second distillation column. The benzoic acid is separated in the second distillation column from the high-boiling components and is drawn off at the column head as the product fraction, whereas the high-boiling components, i.e. those having a higher boiling point than benzoic acid, are drawn off at the column bottom. Such an arrangement of the two columns, in which the benzoic enriched fraction is drawn off from the bottom of the first column and then fed into the second column, is in general referred to as a direct column sequence.

While such a two-column distillation method allows to obtain purified benzoic acid having a high degree of purity, it has major drawbacks. Firstly, this method has an unfavorably high energy consumption, which is due to the fact that two separate distillation columns are needed, which each have to be supplied with the thermal energy required to perform the evaporation of the liquid phase and the separation of the benzoic acid. Even in the best case, the energy consumption amounts to about 750 kWhr/ton of purified benzoic acid. In addition, the plant used in this method has high investment costs. This is not only due to the fact that investment has to be made for two distillation columns, but expenses are also necessary for the further devices associated therewith, such as, for example, condensers, reboilers and pumps. Usually, such a plant comprises two distillation columns, 6 heat exchangers and 5 pumps, i.e. in total 13 main devices. Furthermore, due to the involvement of two distillation columns, a comparable large space is required for the installation of the purification plant.

As an alternative to the aforementioned distillation method making use of a direct column sequence, the abovementioned documents U.S. Pat. No. 3,472,630 and DE 1 443 155 also disclose an inverted arrangement of the two distillation columns. Also in this inverted process, the feed of crude benzoic acid is introduced into the first distillation column, wherein, however, in difference to the direct process, a fraction including the benzoic acid and low-boiling components is drawn off at the column head, while a fraction including the high-boiling components is concentrated at the bottom. The head product enriched in benzoic acid is then condensed and afterwards fed to the second distillation column, which separates the low-boiling components from the benzoic acid. Hence, a fraction including the low-boiling components is drawn off at the head of the second column, whereas the purified benzoic acid is obtained as the bottom product. However, also in this case the energy consumption is high and the investment costs for the plant are high.

The object underlying the present invention is to provide a method for the purification of crude benzoic acid, which overcomes the aforementioned problems, i.e. to provide a method for the purification of crude benzoic acid, which results in benzoic acid with high purity, which has a reduced energy consumption and, which requires a plant with comparable low investment costs.

According to the present invention this object is satisfied by providing a method for purifying a crude benzoic acid containing 5 to 20% by weight of byproducts and 80 to 95% by weight of benzoic acid, by means of distillation, wherein the distillation is performed in a plant comprising a first distillation system, which comprises a divided wall column.

In accordance with the usual definition of the term "divided wall column", the divided wall column preferably comprises:

an upper portion having an upper undivided section for concentrating low-boiling components, wherein the low-boiling components have a lower boiling point than benzoic acid, and an outlet for removal of the low-boiling components from the column, a lower portion having a lower undivided section for concentrating high-boiling components, wherein the high-boiling components have a higher boiling point than benzoic acid, and an outlet for removal of the high-boiling components from the column, and a central portion arranged between the upper portion and the lower portion having at least one vertical dividing wall for dividing the central portion into at least one feed section and at least one withdrawal section, the feed section having an inlet for the feed of crude benzoic acid and the withdrawal section having a side draw outlet for the purified benzoic acid.

This solution is based on the finding that by making use of a divided wall column for the distillation of the crude benzoic acid and by drawing off the purified benzoic acid from the withdrawal section of the central portion of the column, the energy consumption of the method as well as the investment costs for the required plant are significantly reduced, while a purified benzoic acid is obtained, which has at least the same purification degree than that obtained with the distillation methods known in the prior art. More specifically, the energy consumption of the method in accordance with the present invention is about 540 kWhr/ton, which is nearly 30% less than that of the above mentioned methods known in the prior art, which have an energy consumption of about 750 kWhr/ton. Moreover, the plant required to perform the method in accordance with the present invention comprises one divided wall column needing at most 5 heat exchangers and at most 4 pumps, i.e. in total 10 main devices, which is less than the 13 main devices needed for the plant of the above mentioned methods known in the prior art. Nevertheless, the method in accordance with the present invention leads to purified benzoic acid having at least the same degree of purification than that the above mentioned methods known in the prior art.

During the development of the method in accordance with the present invention, the inventor has also tested a method of purifying crude benzoic acid making use of an inverted arrangement of two regular distillation columns, in which crude benzoic acid was fed to the first column, from which a fraction including benzoic acid and low-boiling components was drawn off at the column head and the high-boiling components were separated as bottom product. Then the head fraction including benzoic acid and the low-boiling components was fed to the second column, in which a purified benzoic acid was separated as the bottom product and the low-boiling components were drawn off as the head product. In contrast to the aforementioned prior art methods making use of an inverted two-column arrangement described in documents U.S. Pat. No. 3,472,630 and DE 1 443 155, which comprise the condensation of the head product drawn off from the first column before it is fed into the second column, in the method making use of an inverted arrangement of two regular distillation columns tested by the inventor the head product containing the benzoic acid from the first column was fed directly into the second distillation column as a vapor stream without prior condensation. It was found that—as expected—by feeding the vapor stream obtained in the column head of the first column into the feed of the second column without intermediate condensation, the energy consumption of the method was reduced in comparison to both method alternatives disclosed in the above mentioned prior art documents. However, the degree of reduction in energy consumption is quite low, because this method requires a higher reflux ratio than the two method alternatives disclosed in the above mentioned prior art documents and thus still a comparable high energy demand. Moreover, it was found that the purification degree of the obtained benzoic acid was significantly reduced due to a lower separation ratio of the low-boiling components/benzoic acid.

In light of this, it was surprising that by making use of a divided wall column for the distillation of the crude benzoic acid not only the energy consumption is significantly reduced in comparison to the methods known in the prior art, but that nevertheless benzoic acid with at least the same purification degree is obtained, i.e. that nevertheless the purification efficiency of the process is not deteriorated.

In addition, since two conventional distillation columns are replaced in the method in accordance with the present invention by only one column, namely a divided wall column, the investment costs and the space required for the installation of the purification plant are significantly decreased.

All in all, the method in accordance with the present invention leads to an efficient purification of crude benzoic acid at low operation costs and low investment costs, i.e. results in benzoic acid with high purity, while the method has a reduced energy consumption and requires a plant with comparable low investment costs.

In accordance with the present invention, the term "benzoic acid" not only denotes unsubstituted benzoic acid, i.e. $C_6H_5CO_2H$, but also substituted benzoic acid and in particular benzoic acid, in which one or more hydrogen atoms are replaced by a halogen, such as in particular fluorine, chlorine and/or bromine, a hydroxyl group, a $C_{1-6}$-alkyl group, a $C_{1-6}$-alkoxy group, a nitro group, an aldehyde group, a cyano group or the like. In particular, one hydrogen atom may be replaced by one of the aforementioned groups, wherein the group is for example located at the para-position of the phenyl ring of the benzoic acid.

Benzoic acid with high purity means in this connection a composition including at least 98% by weight of benzoic acid, preferably at least 99% by weight, more preferably at least 99.2% by weight, even more preferably at least 99.4% by weight and most preferably at least 99.5% by weight of benzoic acid based on 100% by weight of the purified benzoic acid stream drawn off from the divided wall column.

As set out above, the divided wall column of the present invention comprises at least one and preferably exactly one vertical dividing wall, which divides the central portion of the column into at least one feed section and one withdrawal section. Vertical means in this connection that the wall is arranged substantially vertical, wherein the angle between the wall and the vertical plane is at most 10°, preferably at most 5°, more preferably at most 2°, even more preferably at most 1° and most preferably 0°.

Preferably, the dividing wall divides the central part of the divided wall column in such a manner that the feed section and the withdrawal section of the central portion of the divided wall column have substantially the same volume, i.e. the area of the cross-section of the central portion of the divided wall column comprises about 50% of the feed section and about 50% of the withdrawal section, wherein about 50% means 30 to 70%, preferably 40 to 60%, more preferably 45 to 65% and most preferably 48 to 52%.

The divided wall column preferably has an essentially cylindrical shape, i.e. the divided wall column has essentially a circular cross-section.

In accordance with a further preferred embodiment of the present invention, the lower, central and upper portions of the divided wall column extend, from the bottom to the top of the column viewed in vertical direction, as follows:

lower portion about 10 to 40%, preferably 15 to 30% and more preferably 22 to 27% based on the total length of the divided wall column, central portion about 20 to 80%, preferably 30 to 70% and more preferably 40 to 60% based on the total length of the divided wall column and upper portion about 10 to 40%, preferably 15 to 30% and more preferably 22 to 27% based on the total length of the divided wall column.

Particularly good results are e.g. achieved with a divided wall column, in which the lower portion extends from 15 to 25%, the central portion extends up to 70% and the upper portion extends from 15 to 25% of the total length of the active mass transfer sections of the column In principle, the present invention is not particularly limited with regard to the dimensions of the divided wall column. The optimum diameter depends e.g. on the desired operating capacity, product purity and operating pressure. However, particularly good results are achieved, if the divided wall column has a circular shape and a diameter between 100 and 6,000 mm, preferably between 200 and 5,000 mm and more preferably between 400 and 4,750 mm. Should the diameter of the column be not constant over the length of the column, the aforementioned diameter is the maximum diameter of the divided wall column.

Moreover, it is preferred that the divided wall column has a length between 2,000 and 30,000 mm, preferably between 2,500 and 25,000 mm and more preferably between 3,000 and 20,000 mm. The optimum length depend in particular from the type of packing used.

A particular advantage of the method in accordance with the present invention is that any crude benzoic acid can be applied as starting material, independent from how it is composed. In particular, the present invention is suitable for purifying crude benzoic acid, which is obtained by oxidation of toluene with oxygen, e.g. in the form of air, in the presence of a transition metal catalyst, such as a cobalt based catalyst or a manganese-based catalyst.

The crude benzoic acid applied as starting material in the method in accordance with the present invention contains 5 to 20% by weight and preferably 10 to 15% by weight of byproducts or 80 to 95% by weight and preferably 85 to 93% by weight of benzoic acid, respectively. The chemical nature and amount of the byproducts depend on the method, with which the crude benzoic acid is prepared. In particular, if it is prepared by oxidation of toluene with oxygen in the presence of a transition metal catalyst, the byproducts include at least one byproduct selected from the group consisting of acetophenone, benzaldehyde, benzyl formate, benzyl acetate, acetic acid, methyl benzoate, fluorenone, toluene, benzyl benzoate, phthalic acid, benzyl alcohol, 2-methyl-diphenyl benzoate, diphenyl benzoate, 2,2-dimethyl-diphenyl benzoate, 2,3-dimethyl-diphenyl benzoate, 3-methyl-diphenyl benzoate, 3,3-dimethyl-diphenyl benzoate and any combinations thereof.

In order to achieve a good separation of the three fractions obtained at the upper, central and lower portion of the divided wall column, while keeping the thermal impact and thus the formation of byproducts during the purification low, the distillation in the divided wall column is preferably carried out in vacuum. Good suppression of byproduct formation and accordingly high yields of purified benzoic acid are in particular obtained, when the pressure and temperature at the bottom of the divided wall column are in the ranges of 50 to 500 mbar and of 120 to 240° C., preferably of 100 to 400 mbar and of 130 to 230° C. and more preferably of 150 to 300 mbar and of 140 to 220° C. and/or when the pressure and temperature at the head of the divided wall column are in the ranges of 55 to 505 mbar and of 125 to 245° C., preferably of 105 to 405 mbar and of 135 to 235° C. and more preferably of 155 to 305 mbar and of 145 to 225° C.

It has been recognized within the present invention that, although the benzoic acid is obtained in the method in accordance with the present invention with an excellently high purity, the product after the distillation in the divided wall column contains a minor amount of benzyl benzoate, which is formed during the distillation by esterification of benzoic acid with the byproduct benzyl alcohol. Moreover, it has been recognized within the present invention that the amount of benzyl benzoate present in the purified product depends on the residence time of the benzoic acid stream in the divided wall column. In order to minimize the amount of benzyl alcohol in the purified product, it is therefore proposed to assure that the residence time of the benzoic acid stream in the divided wall column does not exceed a certain value. More specifically, the method is preferably conducted in a manner that the residence time of benzoic acid in the divided wall column measured in the sump, as it can be accurately measured by means of mass balance measurements using an inert heavy boiler, is between 120 and 1,440 minutes, preferably between 180 and 1,080 minutes and more preferably between 240 and 720 minutes.

The adjustment of the aforementioned residence time of the benzoic acid stream in the divided wall column may be achieved for example by providing in the divided wall column a column boot having a cross-sectional area that is about 15 to 40% of the diameter of the column indicated above.

In addition to the aforementioned embodiment or alternatively to the aforementioned embodiment, the adjustment of the aforementioned residence time of the benzoic acid stream in the divided wall column may be achieved by providing a falling film evaporator and/or a film reboiler in the plant. Due to its particular reduced liquid hold-up, a falling film evaporator is preferred and an agitated (wiped) film reboiler is particularly preferred.

Furthermore, it is preferred that the plant and in particular the first distillation system lacks a device selected from a kettle reboiler, a thermosiphon, a forced circuit reboiler and any combinations thereof, in order to adjust an appropriate residence time of the benzoic acid stream in the divided wall column. This is due to the fact that kettle reboilers, thermosiphons and forced circuit reboilers have a comparable high liquid hold-up, which favors side-reactions leading to benzoylbenzoate.

All in all, by controlling the residence time of the benzoic acid stream in the divided wall column the amount of benzyl benzoate in the purified benzoic acid drawn off from the side draw outlet of the divided wall column is adjusted to less than 0.5% by weight, preferably less than 0.4% by weight, more preferably less than 0.3% by weight and most preferably less than 0.2% by weight based on 100% by weight of the purified benzoic acid.

In accordance with a further preferred embodiment of the present invention, a stream is drawn off at the bottom of the divided wall column, before a portion of the stream is subsequently reboiled and fed back to the divided wall column via a side feed in the lower undivided section. The stream drawn off at the bottom is enriched in high-boiling components and, in addition, this stream contains a small amount of benzoic acid accumulated in the bottom. By feeding back a part of this stream into the divided wall column, it is achieved that at least a part of the withdrawn benzoic acid is reintroduced into the distillation column, thereby increasing the yield of purified benzoic acid since less benzoic acid is finally discharged with the bottom product. Preferably, most of the stream and preferably at least 90% of the stream drawn off at the bottom of the divided wall column is subsequently reboiled and fed back to the divided wall column via a side feed in the lower undivided section.

Due to similar reasons, alternatively to the aforementioned embodiment or, preferably, in addition to the aforementioned embodiment the stream drawn off at the head of the divided wall column may be subsequently condensed, before a portion of the obtained condensate is fed back to the divided wall column via a side feed into the upper undivided section. This stream drawn off at the head is enriched with low boiling components and contains a small amount of benzoic acid accumulated in the head. Thus, similarly to the recycling of the bottom stream, partially feeding back the stream drawn off at the head also leads to an increase of the yield of the purified benzoic acid. Preferably, 70 to 99% of the stream drawn off at the head of the divided wall column is subsequently condensed and fed back to the head of the divided wall column via a side inlet. Alternatively, an internal reflux could be used.

In order to achieve an appropriate separation efficiency during the distillation in the divided wall column, a separation means or separation aid, respectively, is preferably arranged in at least one of the upper undivided section, the lower undivided section, the feed section and the withdrawal section and more preferably in all of the upper undivided section, the lower undivided section, the feed section and the withdrawal section. The present invention is not particularly limited with regard to the type of separation means or separation aid, respectively. Good results are obtained by using a suitable separation means selected from the group consisting of trays, random packings, structured packings and any combinations thereof. A particularly good separation efficiency is obtained, when a structured packing is used as the separation means. Most preferably, structured packings having a specific surface area in the range of 125 to 900 $m^2/m^3$, preferably of 200 to 750 $m^2/m^3$ and more preferably of 250 to 500 $m^2/m^3$ are used. A particular advantage of the use of structured packings is that this allows a compact design of the divided wall column and reduces the liquid hold-up. Structured packings, which have turned out to provide an excellent separation efficiency in the distillation of benzoic acid in a divided wall column, are the Sulzer Chemtech Mellapak-Plus™ packings.

In order to achieve a significantly low energy consumption, the first distillation system and preferably the whole plant does in accordance with a particular preferred embodiment of the present invention not comprise any further distillation column in addition to the divided wall column.

On the other hand, from the viewpoint of the separation efficiency achieved by the distillation in the divided wall column it may be in certain cases advantageous to remove certain low-boiling components from the crude benzoic acid before it is fed to the divided wall column. Therefore, it is considered that in certain cases it might be advantageous to subject the crude benzoic acid to a distillation in a second distillation system prior to the distillation in the first distillation system, wherein the distillation in the second distillation system is performed so that low-boiling components, such as e.g. those selected from the group consisting of water, toluene, catalyst and a combination thereof, are removed from the crude benzoic acid before it is fed to the first distillation system. Since in this embodiment at least a part of the low-boiling components has already been removed in the second distillation system before the benzoic acid is further purified in the first distillation system, the time required for the purification of the benzoic acid in the first distillation system and thus in particular the residence time in the divided wall column may be reduced. As a consequence, the formation of byproducts is reduced which results in a higher yield of benzoic acid. For example, the second distillation system may comprise one to three and for instance either two or three distillation columns, wherein the distillation columns of the second distillation system preferably do not have a dividing wall. For the sake of completeness, it is noted that the distillation column(s) of the second distillation system are pre-columns, which are usually used in the prior art plants to remove light boilers, such as water and/or toluene.

In particular for the aforementioned embodiment, it is preferred that the crude benzoic acid, which is fed to the second distillation system, is prepared by an oxidative reaction of toluene and oxygen in the presence of a transition metal catalyst, preferably a cobalt-based catalyst.

With the aforementioned embodiments, benzoic acid having a purity of at least 98% by weight, preferably of at least 99% by weight, more preferably at least 99.2% by weight, even more preferably at least 99.4% by weight and most preferably at least 99.5% is obtained.

Although the distillation of a crude benzoic acid in a divided wall column as described above leads to a highly purified benzoic acid product, in certain specific cases, such as for the use of the benzoic acid in food-grade or pharmaceutical-grade applications, an even higher purity is required for the benzoic acid.

If benzoic acid with such a high purity e.g. for the use in food-grade or pharmaceutical-grade applications is required, it is suggested in accordance with another particularly preferred embodiment of the present invention to subject the purified benzoic acid stream withdrawn from the side draw outlet of the divided wall column subsequently to a further purification step, which preferably comprises at least one melt crystallization step.

By performing at least one melt crystallization step subsequently to the distillation in the divided wall column, a further purification of the benzoic acid product is obtained. More specifically, with this embodiment benzoic acid containing at least 99.6% by weight of benzoic acid, preferably at least 99.7% by weight of benzoic acid, more preferably at least 99.9% by weight of benzoic acid and most preferably at least 99.95% by weight of benzoic acid based on 100% by weight of the further purified benzoic acid product is obtained.

After the distillation in the divided wall column the purified benzoic acid stream, which is then subjected to the melt crystallization process, may comprise minor amounts of byproduct selected from the group consisting of benzyl benzoate, phthalic acid, benzyl alcohol, 2-methyl-diphenyl benzoate, diphenyl benzoate, 2,2-dimethyl-diphenyl benzoate, 2,3-dimethyl-diphenyl benzoate, 3-methyl-diphenyl benzoate, 3,3-dimethyl-diphenyl benzoate and any combinations thereof. Melt crystallization is particularly suitable to significantly reduce the amount of these byproducts.

In order to obtain a particular good purification, the melt crystallization is preferably performed by a static crystallization, a dynamic crystallization or a combination thereof. For this purpose, any type of static crystallizers and/or of dynamic crystallizers known to a person skilled in the art may be used. A particular preferred example for a dynamic crystallizer is a falling film crystallizer.

Apart from leading to a high product yield, static crystallization has the advantage of high flexibility, of wide operating range, of easy operation since there is no crystal slurry handling and no filtration, of high reliability and of low operation costs due to the lack of moving parts.

Falling film crystallization leads to a high product yield and is characterized by an easy operation since there is no crystal slurry handling and no filtration, by a high reliability and by low operation costs. Falling film crystallization is advantageously faster than static crystallization.

In accordance with a very preferred embodiment of the present invention, a benzoic acid product having an excellently high purity is obtained by performing the melt crystallization after the distillation in the divided wall column by means of a combination of falling film crystallization and static crystallization. In addition to the provision of a highly pure benzoic acid product, the method in accordance with this embodiment leads to a higher yield of the purified benzoic acid with less amounts of benzoic acid remaining in the crystallization residue. Moreover, this combination of crystallization steps leads to investment and operation cost savings due to optimized process integration and allows a highly flexible operation. In particular, the provision of a falling film crystallization (also suspension crystallization) allows for a reduction of the residence time in the divided wall column with the advantages connected therewith as set out above.

Preferably, the static crystallization step is performed downstream of the falling film crystallization step.

In accordance with a particular preferred embodiment of the present invention, downstream of the divided wall column a falling film crystallizer is arranged and downstream of the falling film crystallizer a static crystallizer is arranged. Preferably, the combination of falling film crystallization and static crystallization is performed in a specific arrangement of a falling film crystallizer and a static crystallizer, wherein the purified benzoic acid stream from the side draw outlet of the divided wall column is introduced into a falling film crystallizer which is connected with a first circuit line, which is e.g. connected with an outlet line for purified benzoic acid. In addition, the static crystallizer located downstream of the falling film crystallizer is provided with a second circuit line, which connects the static crystallizer with the falling film crystallizer. Furthermore, the static crystallizer is provided with an outlet line for removing the residue of the benzoic acid purification. During the operation of this plant, benzoic acid drawn off from the divided wall column is introduced into a first falling film crystallizer, in which a first crystallization of the benzoic acid is performed to produce a second purified benzoic acid stream and a first residue stream, which is fed to the static crystallizer. The purity of the second purified benzoic acid stream is increased by feeding it to a second falling film crystallizer to form a third purified benzoic acid stream (the purified product typically having a pharmaceutical grade purity) and a second residue stream. The second residue stream will typically be fed back to the first falling film crystallizer to increase the yield. The purity of the first residue from the first falling film crystallizer is further increased by a static crystallization step. While the third residue from the static crystallization, which contains mainly byproducts, is drawn off from the static crystallizer via the respective outlet line, the purified product of the static crystallization is fed back to the first falling film crystallizer. This embodiment is particularly useful in the production of pharmaceutical grades, such as those having a purity of more than 99.95% by weight.

In accordance with still another embodiment of the present invention, a portion of the residue, which is obtained in the static crystallization and drawn off from the static crystallizer, may be fed back to the distillation in the divided wall column. For example, 50 to 70% by weight of the residue may be reintroduced into the distillation of the divided wall column. Such a recycling of the residue leads to an increase of the overall yield of purified benzoic acid.

The method according to the aforementioned embodiments making use of at least one melt crystallization step subsequent to the distillation in the divided wall column leads to a purified benzoic acid product including at least 99.5% by weight, preferably at least 99.6% by weight, more preferably at least 99.7% by weight, even more preferably at least 99.8% by weight, still more preferably at least 99.9% by weight and most preferably at least 99.9% by weight of benzoic acid.

In accordance with a further aspect, the present invention relates to a plant for purifying a crude benzoic acid, wherein the plant comprises a first distillation system, which comprises a divided wall column, and downstream thereof at least one crystallizer.

Preferably, the at least one crystallizer is selected from the group consisting of suspension crystallizers, static crystallizers, falling film crystallizers and combinations thereof.

In accordance with a particular preferred embodiment of the present invention, downstream of the divided wall column a falling film crystallizer is arranged and downstream of the falling film crystallizer a static crystallizer is arranged. This embodiment is particularly preferred when the purity of the benzoic acid product from the divided wall column is quite high, such as more than 99%.

In the most preferred embodiment, e.g. for a benzoic acid product from the divided wall column having a purity of less than 99%, downstream of the divided wall column a first and a second falling film crystallizers are arranged and downstream of the falling film crystallizers a static crystallizer is arranged.

In accordance with still a further aspect, the present invention relates to a plant for purifying a crude benzoic acid by means of distillation, in particular for carrying out the above described method, wherein the plant comprises:
i) a supply of oxygen or compressed air,
ii) a supply of transition metal catalyst,
iii) a supply containing toluene and
iv) a reactor for the partial oxidation of toluene with oxygen to form crude benzoic acid, which has at least two inlets and an outlet,
wherein the supply of oxygen or compressed air, the supply of transition metal catalyst and the supply containing toluene are all in fluid communication with the reactor for feeding oxygen or compressed air, transition metal catalyst and toluene to the reactor, wherein a first distillation system, which comprises a divided wall column, is in fluid communication with the outlet of the reactor for the partial oxidation of toluene with oxygen to form crude benzoic acid.

Preferably, the reactor for the partial oxidation of toluene with oxygen to form crude benzoic acid is a loop reactor.

In a further development of the present invention, it is suggested that the supply of transition metal catalyst and the supply containing toluene are each connected by means of a supply line with one feed line, which is connected with one inlet of the reactor for the partial oxidation of toluene with oxygen to form crude benzoic acid, so that during the operation of the plant a mixture of catalyst and toluene is introduced into the reactor for the partial oxidation of toluene with oxygen to form crude benzoic acid.

The central portion of the divided wall column, which is divided by the wall into two sides, may be either symmetric or unsymmetric concerning the height ratio of the single upper (rectifying) sections and lower (stripping) sections of both sides of the central portion of the divided wall column and/or concerning the number of beds located in the single upper (rectifying) sections and lower (stripping) sections of both sides of the central portion of the divided wall column. In particular, the two upper and lower sections of the central portion may each comprise one or more beds. The bed height corresponds to the total packing height of that section and each bed may consist of one or more packing layers. For example, the upper section of the feed side may consist of two beds and its lower side may consist of a single bed, whereas the upper section of the withdrawal side may consists of a single bed and its lower side may consist of three beds.

It has been surprisingly found in the present invention that for purifying a crude benzoic acid the feed side has a height ratio of the upper to lower section of preferably from 0.66 to 1.5, more preferably from 0.8 to 1.2 and most preferably from 0.9 to 1.1. It has been further found in the present invention that the optimum height ratio on the withdrawal side depends on the composition of the feed to the divided wall column. It has been further found that as the purity of the feed (crude benzoic acid) decreases, for example, due to a higher concentration of 2-methylbiphenyl and 4-methylbiphenyl, the height ratio on the withdrawal side should be increased, and the height of the upper portion is in this case preferably greater than that of the lower portion. The optimum height ratio on the withdrawal side thus varies depending primarily on the purity of the feed. The inventor has furthermore surprisingly found that for most typical crude benzoic acids, a suitable height ratio on the withdrawal side is preferably from about 0.2 to about 0.35, more preferably from about 0.25 to about 0.3 and most preferably about 0.28.

Also in this aspect of the present invention, it is preferred that downstream of the first distillation system at least one crystallizer is provided.

Preferably, the at least one crystallizer is selected from the group consisting of suspension crystallizers, static crystallizers, falling film crystallizers and combinations thereof.

In accordance with a particular preferred embodiment of the present invention, downstream of the divided wall column a falling film crystallizer is arranged and downstream of the falling film crystallizer a static crystallizer is arranged. This embodiment is particularly preferred when the purity of the benzoic acid product from the divided wall column is quite high, such as more than 99%.

In the most preferred embodiment, e.g. for a benzoic acid product from the divided wall column having a purity of less than 99%, downstream of the divided wall column a first and a second falling film crystallizers are arranged and downstream of the falling film crystallizers a static crystallizer is arranged.

Specific embodiments in accordance with the present invention are now described with reference to the appended drawings and by an example.

FIG. 3 shows a post purification device to be used downstream of a divided wall column as shown e.g. in FIG. 1 or FIG. 2 in accordance with a third embodiment of the present invention.

FIGS. 4A and B show two examples for divided wall column for a plant for conducting the method for purifying benzoic acid in accordance with other embodiments of the present invention.

Figure 1:
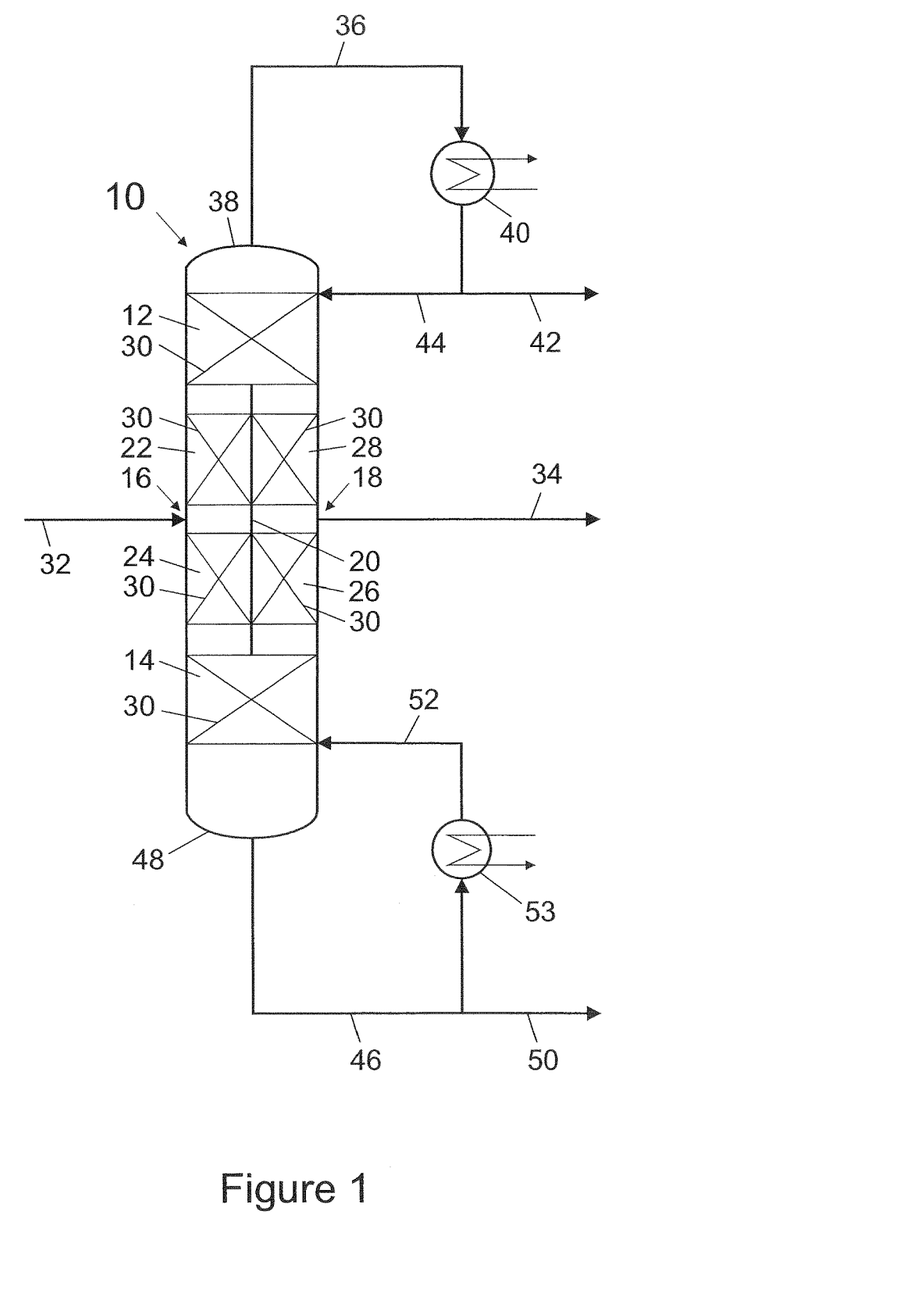
FIG. 1 shows a plant for conducting the method for purifying benzoic acid in accordance with a first embodiment of the present invention.

FIG. 1 shows a plant for conducting the method for purifying benzoic acid in accordance with one embodiment of the present invention. This plant comprises only one distillation column, namely a cylindrical divided wall column 10 for purifying benzoic acid by distillation having a height of 22,500 mm and a diameter of 1,500 mm. This divided wall column 10 includes an upper portion having an upper undivided section 12, a lower portion having a lower undivided section 14 and a central portion, which is located between the upper portion and the lower portion of the column and which is separated by a vertical wall 20 into a feed section 16 and a withdrawal section 18. More specifically, the vertical wall 20 divides the central portion of the divided wall column 10 in such a manner that the feed section 16 and the withdrawal section 18 have substantially the same volume. Both of the upper undivided section 12 and the lower undivided section 14 consists of one structured packing, such as one of the Sulzer Chemtech series Mellapak Plus™, such as Mellapak Plus™ 452Y. In contrast to this, the central portion comprises four structured packings, such as of the Sulzer Chemtech series Mellapak Plus™, such as Mellapak Plus™ 452Y, wherein one of these four structured packings defines the rectifying section 22 of the feed section 16, another one of these four structured packings defines the stripping section 24 of the feed section 16, another one of these four structured packings defines the stripping section 26 of the withdrawal section 18 and the last one of these four structured packings defines the rectifying section 28 of the withdrawal section 18.

During the operation of this plant, a stream of crude benzoic acid 32 is continuously fed through an inlet into the feed section 16 between the rectifying section 22 and the stripping section 24 of the central portion of the divided wall column 10. The crude benzoic acid 32 may have been obtained, by way of example, by oxidation of toluene with air and usually contains a plurality of byproducts, such as one or more compounds selected from the group consisting of acetophenone, benzaldehyde, benzyl formate, benzyl acetate, acetic acid, methyl benzoate, fluorenone, toluene, benzyl benzoate, phthalic acid, benzyl alcohol, 2-methyldiphenyl benzoate, diphenyl benzoate, 2,2-dimethyl-diphenyl benzoate, 2,3-dimethyl-diphenyl benzoate, 3-methyl-diphenyl benzoate, 3,3-dimethyl-diphenyl benzoate and any combinations thereof. Typically, the crude benzoic acid 32 comprises 5 to 20% by weight of the aforementioned byproducts and usually 10 to 15% by weight of the aforementioned byproducts.

The column is operated at a head pressure, at a bottom pressure, at a head temperature and at a bottom temperature, so that a product stream of purified benzoic acid 34 with a purity of at least 98% by weight and preferably of at least 99% by weight is drawn off from the withdrawal section 18 through the side draw outlet, which is provided between the stripping section 26 and the rectifying section 28. The low-boiling components, i.e. the compounds having a boiling point, which is lower than that of benzoic acid, concentrate during the distillation in the upper undivided section 12, and are drawn off through the column head 38 as a head stream 36, which is subsequently condensed in the condenser 40. The condensed head stream is then divided into a stream of low-boiling components 42, which is discharged from the distillation system, and into a recycle stream of low-boiling components 44, which is fed back to the upper undivided section 12 via a side inlet. The high-boiling components, i.e. the compounds having a boiling point, which is higher than that of benzoic acid, are concentrated in the lower undivided section 14 and drawn off as a bottom stream 46 through the column bottom 48. The bottom stream is subsequently divided into a stream of high-boiling components 50, which is drawn off from the distillation plant, and a recycle stream of high-boiling components 52, which is reboiled in the reboiler 53 and fed back to the lower undivided section 14 via a side inlet.

Figure 2:
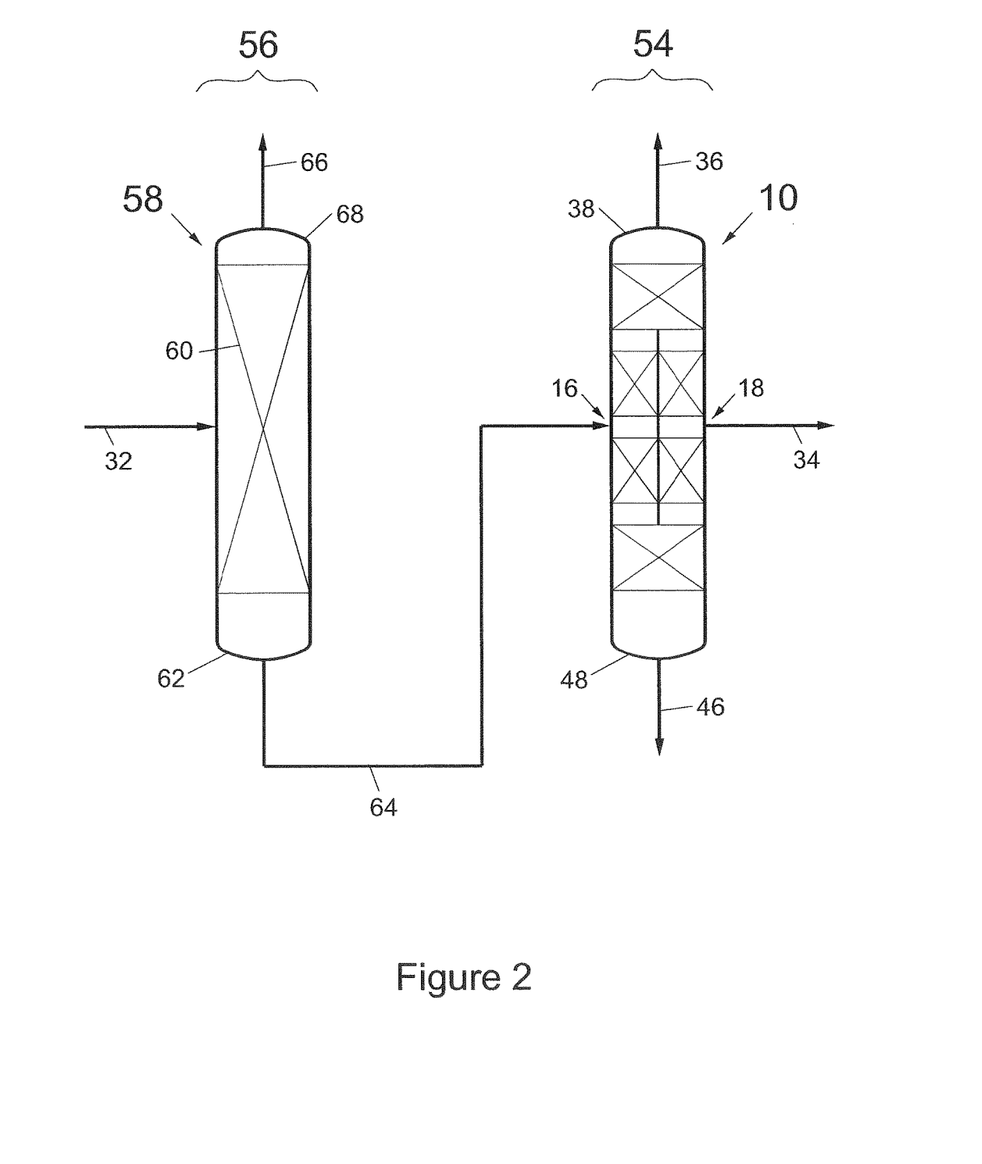
FIG. 2 shows a plant for conducting a method for purifying benzoic in accordance with a second embodiment of the present invention.

FIG. 2 shows a plant for conducting a method for purifying benzoic in accordance with a second embodiment of the present invention. In contrast to the above mentioned first embodiment, this plant in accordance with a second embodiment of the present invention comprises a first distillation system 54, which is a divided wall column as shown in FIG. 1 and as described above with regard to FIG. 1, as well as a second distillation system 56, which is arranged upstream of the first distillation system 54. The second distillation system 56 comprises as a pre-distillation column 58 a conventional distillation column of cylindrical shape, i.e. a distillation column, which does not comprise a dividing wall. A structured packing 60 is provided in the internal volume of the pre-distillation column 58, wherein this structured packing 60 may comprise one or more layers of the same or of different structured packings 60, such as one or more layers of the Sulzer Chemtech structured packing series Mellapak Plus™, such as Mellapak Plus™ 452Y. The bottom 62 of the pre-distillation column 58 and the feed section 16 of the divided wall column 10 are connected via a transfer pipe 64.

During the operation of this plant, a stream of crude benzoic acid 32 is fed to the pre-distillation column 58, which is operated at a head pressure, at a bottom pressure, at a head temperature and at a bottom temperature, so that a part of the low-boiling components, namely mainly toluene and water, is separated and drawn off as a head stream 66 through the column head 68. Benzoic acid is concentrated in the pre-distillation column 58 and drawn off through the bottom 62 together with unseparated byproducts as a bottom stream. This bottom stream is then fed to the feed section 16 of the divided wall column 10 via the transfer pipe 64. The purified benzoic acid stream 34 is then withdrawn from the withdrawal section 18, whereas a head stream 36 comprising the low-boiling components is removed through the column head 38 and a bottom stream 46 containing the high-boiling components is discharged through the bottom 48 of the divided wall column.

Figure 3:
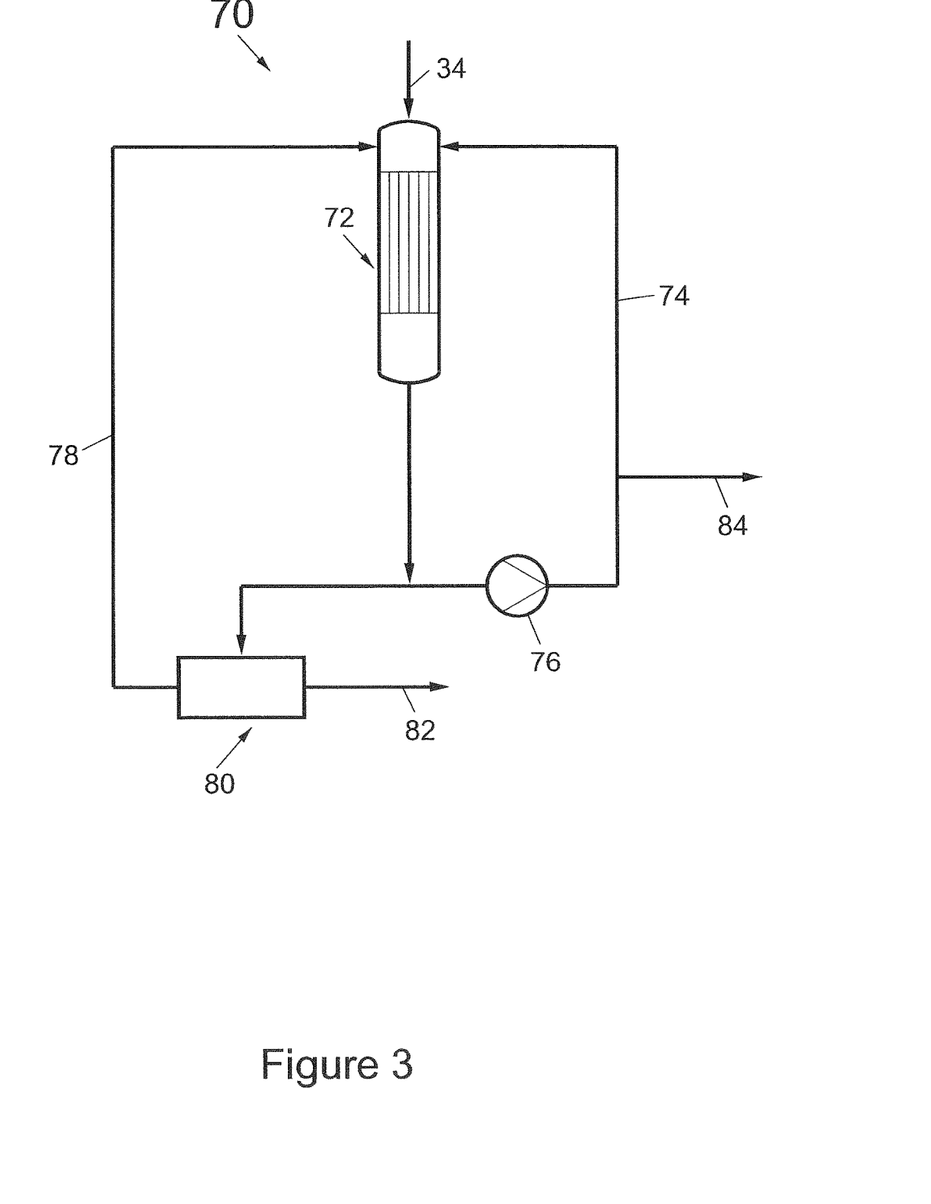

FIG. 3 shows a part of a plant for conducting a method for purifying benzoic in accordance with a third embodiment of the present invention, namely the post purification device located downstream of the divided wall column. Such a plant is advantageously used for the purification of crude benzoic acid in a case that a further purification of the benzoic acid is required after the distillation. The benzoic acid stream 34 purified by distillation with and drawn off from a plant, namely e.g. one as shown in FIG. 1 or as shown in FIG. 2, is charged in this embodiment into a melt crystallizer 70. The melt crystallizer 70 comprises a falling film crystallizer 72, which is connected with a first circuit line 74, which is provided with a pump 76 and connected with an outlet line for purified benzoic acid 84. In addition, the melt crystallizer 70 comprises a static crystallizer 80 located downstream of the falling film crystallizer 72 and is provided with a second melt circuit line 78, which connects the static crystallizer 80 with the falling film crystallizer 72. Furthermore, the static crystallizer 80 is provided with an outlet line for removing the residue 82 of the benzoic acid purification.

During the operation, benzoic acid drawn off from line 34 of the purification plant shown in FIG. 1 or from line 34 of the purification plant shown in FIG. 2 is introduced into the falling film crystallizer 72, in which a first crystallization of the benzoic acid is performed. The resulting melt, which is further enriched in benzoic acid, is drawn off from the bottom of the falling film crystallizer 72 and subsequently divided into two partial streams. A first partial stream of the melt is led into the feed of a static crystallizer 80, in which the purity of the benzoic acid is further increased by a static crystallization step. While the residue 82 from the static crystallization, which contains mainly byproducts, is drawn off from the static crystallizer 80 via the outlet line, the purified benzoic acid melt is fed back to the falling film crystallizer 72 via the second circuit line 78. A second partial stream of the melt drawn off from the bottom of the falling film crystallizer 72 is fed back to the head part of the falling film crystallizer 72 via the first circuit line 74, wherein a stream of the final, further purified benzoic acid 84 having a purity of more than 99.95% by weight, which is the final product of the combined distillation and melt crystallization process, is branched off from the stream recirculated through the first circulation circuit 74.

Figure 4:
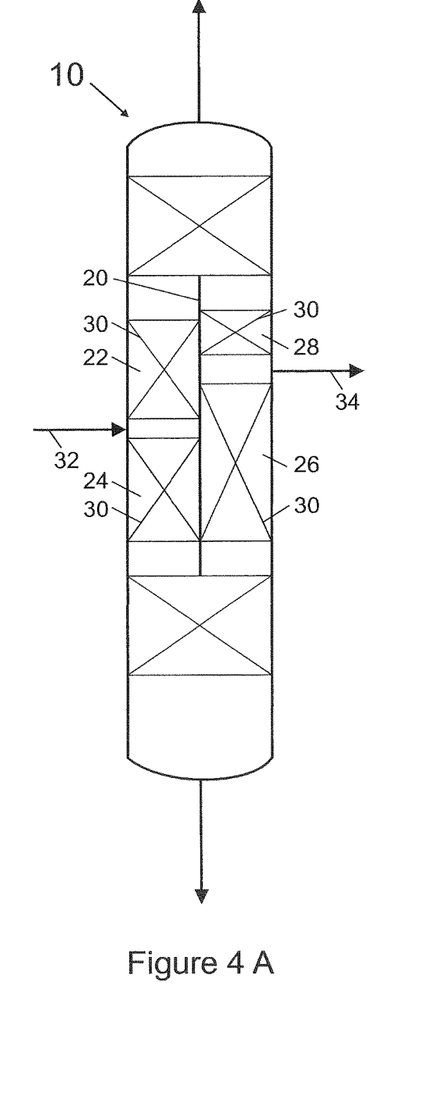

FIGS. 4A and 4B show details of two divided wall columns 10 in accordance with preferred embodiments of the present invention. More specifically, FIGS. 4A and B illustrate "unsymmetrical" divided wall columns 10.

In these embodiments, each side of the central portion of the divided wall column 10, which is located between the upper section 12 and the lower section 14, consists of two sections, namely an upper and a lower section.

The upper section on the feed side or the withdrawal side corresponds to the rectifying portion 22, 28 of that column side 16, 18 and the lower section corresponds to the stripping portion 24, 26 of that column side 16, 18. Here an "unsymmetrical" divided wall column 10 refers to the fact that the height ratio of the upper (rectifying) section 22, 28 to the lower (stripping) section 24, 26 is different on each column side (e.g. feed versus withdrawal side) 16, 18.

The two (upper and lower) sections of the central portion may each comprise one or more beds. The bed height corresponds to the total packing height of that section, and each bed may consist of one or more packing layers. FIG. 4A shows that the upper and lower section on each side 16, 18 has just one single bed. In contrast to this, FIG. 4B illustrates that each of the upper and lower sections on each side has a different number of beds. In the embodiment of FIG. 4B the upper section of the feed side 16 consists of two beds and its lower side consists of a single bed; whereas the upper section of the withdrawal side 18 consists of a single bed and its lower side consists of three beds.

It has been surprisingly found in the present invention that for purifying a crude benzoic acid the feed side has a height ratio of the upper to lower section of preferably from 0.66 to 1.5, more preferably from 0.8 to 1.2 and most preferably from 0.9 to 1.1. It has been further found in the present invention that the optimum height ratio on the withdrawal side 18 depends on the composition of the feed to the divided wall column. It has been further found that as the purity of the feed (crude benzoic acid) decreases, for example, due to a higher concentration of 2-methylbiphenyl and 4-methylbiphenyl, the height ratio on the withdrawal 18 side should be increased, and the height of the upper portion may actually be greater than that of the lower portion. The optimum height ratio on the withdrawal side 18 thus varies depending primarily on the purity of the feed. The inventor has furthermore surprisingly found that for most typical crude benzoic acids, a suitable height ratio on the withdrawal side is preferably from about 0.2 to about 0.35, more preferably from about 0.25 to about 0.3 and most preferably about 0.28.

Subsequently, the present invention is described by means of an illustrative, but not limiting example.

EXAMPLE

The following example is based on a computer simulation (SIMSCI PRO II) using in-house VLE data.

A liquid crude benzoic acid stream has been purified with a plant as shown in FIG. 1. The liquid crude benzoic acid stream had the following composition:
traces of toluene,
1% by weight of acetophenone,
6% by weight of benzaldehyde,
0.001% by weight of benzyl formate,
0.5% by weight of benzoyl alcohol,
0.001% by weight of benzyl acetate,
87.4% by weight of benzoic acid,
0.4% by weight of biphenyl,
0.001% by weight of 2-methylbiphenyl,
0.001% by weight of succinic anhydride,
0.001% by weight of 4-methylbiphenyl,
0.6% by weight of diphenylmethane,
0.001% by weight of 3-methylbiphenyl,
0.001% by weight of phthalic anhydride,
3.993% by weight of benzyl benzoate and
0.1% by weight of benzyl.

A liquid stream of crude benzoic acid with the aforementioned composition has been continuously introduced into the divided wall column 10 via an inlet into the feed section with a mass flow rate of 8,329 kg/h. The distillation was carried out at a pressure in the column bottom of 240 mbar and a bottom temperature of 209° C. The pressure at the column head was 200 mbar and the temperature was 191° C. 3,900 kg/h of a purified benzoic acid stream were drawn off through the side draw outlet of the withdrawal section. The purified benzoic acid stream was composed of 99.52% by weight of benzoic acid and contained 0.1% by weight of biphenyl, 0.17% by weight of diphenyl methane, 0.20% by weight of benzyl benzoate and 0.01% by weight of combined further low-boiling and high-boiling products based on 100% by weight of the purified benzoic acid stream.

The energy consumption was as low as 540 kWhr/ton of purified benzoic acid product.

REFERENCE NUMERAL LIST 10 divided wall column
12 upper undivided section
14 lower undivided section
16 feed section
18 withdrawal section
20 vertical dividing wall
22 rectifying section of the feed section
24 stripping section of the feed section
26 stripping section of the withdrawal section
28 rectifying section of the withdrawal section
30 structured packing
32 crude benzoic acid stream
34 purified benzoic acid stream
36 head stream
38 column head
40 condenser
42 product stream of low-boiling components
44 recycle stream of low-boiling components
46 bottom stream
48 column bottom
50 product stream of high-boiling components
52 recycle stream of high boiling components
53 reboiler
54 first distillation system
56 second distillation system
58 pre-distillation column
60 structured packing of the pre-distillation column
62 bottom of the pre-distillation column
64 transfer pipe
66 head stream of the pre-distillation column
68 head of the pre-distillation column
70 melt crystallizer
72 falling film crystallizer
74 first circuit line
76 pump
78 second circuit line
80 static crystallizer
82 residue
84 further purified benzoic acid stream

The invention claimed is:

1. A method for purifying a crude benzoic acid stream containing 5 to 20% by weight of byproducts and 80 to 95% by weight of benzoic acid, by means of distillation, the method comprising delivering the crude benzoic acid stream to a plant comprising a first distillation system, wherein the first distillation system comprises a divided wall column, thereby providing a purified benzoic acid stream.

2. The method of claim 1, wherein the divided wall column comprises:
an upper portion having an upper undivided section for concentrating low-boiling components, wherein the low-boiling components have a lower boiling point than benzoic acid, and an outlet for removal of the low-boiling components from the divided wall column,
a lower portion having a lower undivided section for concentrating high-boiling components, wherein the high-boiling components have a higher boiling point than benzoic acid, and an outlet for removal of the high-boiling components from the divided wall column, and
a central portion arranged between the upper portion and the lower portion having at least one vertical dividing wall for dividing the central portion into at least one feed section and at least one withdrawal section, the feed section having an inlet for the feed of crude benzoic acid and the withdrawal section having a side draw outlet for the purified benzoic acid.

3. The method of claim 2, wherein a separation means is arranged in at least one of the upper undivided section, the lower undivided section, the feed section and the withdrawal section.

4. The method of claim 3, wherein the separation means is selected from the group consisting of trays, random packings, structured packings and any combinations thereof.

5. The method of claim 3, wherein the separation means is a structured packing having a specific surface area in the range of 125 to 900 m2/m3.

6. The method of claim 1, wherein the crude benzoic acid introduced into the divided wall column comprises 5 to 20% by weight of at least one byproduct selected from the group consisting of acetophenone, benzaldehyde, benzyl formate, benzyl acetate, acetic acid, methyl benzoate, fluorenone, toluene, benzyl benzoate, phthalic acid, benzyl alcohol, 2-methyl-diphenyl benzoate, diphenyl benzoate, 2,2-dimethyl-diphenyl benzoate, 2,3-dimethyl-diphenyl benzoate, 3-methyl-diphenyl benzoate, 3,3-dimethyl-diphenyl benzoate and any combinations thereof.

7. The method of claim 1, wherein a pressure and a temperature at a bottom of the divided wall column are in the ranges of 50 to 500 mbar and 120 to 240° C.

8. The method of claim 1, wherein a pressure and a temperature at a head of the divided wall column are in the ranges of 55 to 505 mbar and 125 to 245° C.

9. The method of claim 1, wherein a residence time of benzoic acid in the divided wall column measured in the sump is between 120 and 1,440 minutes.

10. The method of claim 9, wherein the divided wall column comprises a column boot having a cross-sectional area that is about 15 to 40% of a diameter of the divided wall column.

11. The method of claim 9, wherein the plant comprises at least one of a falling film evaporator and a film reboiler.

12. The method of claim 1, wherein the first distillation system does not include any further distillation column in addition to the divided wall column.

13. The method of claim 1, wherein the crude benzoic acid is subjected to a distillation in a second distillation system prior to the distillation in the first distillation system, wherein the distillation in the second distillation system is performed so that low-boiling components selected from the group consisting of water, toluene, catalyst and a combination thereof are removed from the crude benzoic acid before it is fed to the first distillation system.

14. The method of claim 1, wherein the purified benzoic acid stream removed from the divided wall column is subjected to a further purification step, which comprises at least one melt crystallization step.

15. The method of claim 14, wherein the further purification step is a suspension crystallization, a static crystallization, a falling film crystallization or a combination thereof.

16. The method of claim 15, wherein the at least one melt crystallization step is a combination of a falling film crystallization and a static crystallization, wherein the purified benzoic acid stream removed from the divided wall column is first introduced into a falling film crystallizer and thereafter a residue from the falling film crystallizer is introduced into a static crystallizer.

17. A plant for purifying a crude benzoic acid by means of distillation, the plant comprising:
   i) a supply line containing oxygen or compressed air,
   ii) a supply line containing transition metal catalyst,
   iii) a supply line containing toluene and
   iv) a reactor for the partial oxidation of toluene with oxygen for form crude benzoic acid, the reactor having at least two inlets and an outlet,
   wherein the supply line containing oxygen or compressed air, the supply line containing transition metal catalyst and the supply line containing toluene are all in fluid communication with the reactor for feeding oxygen or compressed air, transition metal catalyst and toluene to the reactor, wherein a first distillation system, which comprises a divided wall column, is in fluid communication with the outlet of the reactor for the partial oxidation of toluene with oxygen to form crude benzoic acid.

18. The plant of claim 17, wherein the plant is configured to carry out a method for purifying a crude benzoic acid containing 5 to 20% by weight of byproducts and 80 to 95% by weight of benzoic acid, by means of distillation.

* * * * *